(12) United States Patent
McGuire, Jr.

(10) Patent No.: US 10,314,935 B2
(45) Date of Patent: Jun. 11, 2019

(54) CHLORHEXIDINE-CONTAINING ANTIMICROBIAL LAMINATES

(75) Inventor: James E. McGuire, Jr., Tiburon, CA (US)

(73) Assignee: entrotech life sciences, inc., San Francisco, CA (US)

(*) Notice: Subject to any disclaimer, the term of this patent is extended or adjusted under 35 U.S.C. 154(b) by 0 days.

(21) Appl. No.: 13/140,104

(22) PCT Filed: Jan. 7, 2010

(86) PCT No.: PCT/US2010/020402
§ 371 (c)(1),
(2), (4) Date: Jul. 29, 2011

(87) PCT Pub. No.: WO2010/080936
PCT Pub. Date: Jul. 15, 2010

(65) Prior Publication Data
US 2011/0290259 A1 Dec. 1, 2011

Related U.S. Application Data

(60) Provisional application No. 61/142,896, filed on Jan. 7, 2009.

(51) Int. Cl.
*A61B 19/00* (2006.01)
*A61L 15/46* (2006.01)
(Continued)

(52) U.S. Cl.
CPC .............. *A61L 15/46* (2013.01); *A61B 46/40* (2016.02); *A61B 2017/00889* (2013.01);
(Continued)

(58) Field of Classification Search
CPC ........ A61F 2013/0091; A61L 2300/206; A61L 2300/404; A61B 2017/00889; A61B 2019/085
(Continued)

(56) References Cited

U.S. PATENT DOCUMENTS 2,684,924 A 7/1954 Rose et al.
2,804,073 A 8/1957 Gallienne et al.
(Continued)

FOREIGN PATENT DOCUMENTS

CN 101322661 12/2008
EP 0 196 459 10/1986
(Continued)

OTHER PUBLICATIONS

"3M DuraPrep Surgical Solution—Patient Preoperative Skin Preparation," *3M Technical Brochure*, (3M Company, St. Paul, MN), (Sep. 29, 2006).
(Continued)

*Primary Examiner* — Ophelia A Hawthorne
*Assistant Examiner* — Caitlin A Carreiro
(74) *Attorney, Agent, or Firm* — The Griffith Law Firm, A P.C.; Lisa M. Griffith (57) ABSTRACT

Antimicrobial laminates of the invention include at least one adhesive layer; a backing outwardly exposed on a first side of the adhesive layer; and, optionally, a release liner outwardly exposed on a second side of the adhesive layer opposite from the first side of the adhesive layer. At least one of the at least one adhesive layer and the backing includes an antimicrobially effective amount of substantially pure chlorhexidine.

20 Claims, 2 Drawing Sheets

(51) Int. Cl.
*A61B 46/00* (2016.01)
*A61B 17/00* (2006.01)
*A61F 13/00* (2006.01)
*A61B 46/20* (2016.01)

(52) U.S. Cl.
CPC . *A61B 2046/205* (2016.02); *A61F 2013/0091* (2013.01); *A61F 2013/00604* (2013.01); *A61L 2300/216* (2013.01); *A61L 2300/404* (2013.01)

(58) Field of Classification Search
USPC .............. 128/849; 602/52, 57; 424/443, 447
See application file for complete search history.

(56) References Cited

U.S. PATENT DOCUMENTS

| | | | |
|---|---|---|---|
| 2,884,126 | A | 4/1959 | Ulrich |
| 3,577,516 | A | 5/1971 | Gould et al. |
| 3,608,070 | A | 9/1971 | Nouvel |
| 3,932,607 | A | 1/1976 | Hesselgren |
| 3,975,350 | A | 8/1976 | Hudgin et al. |
| 4,181,752 | A | 1/1980 | Martens et al. |
| 4,310,509 | A | 1/1982 | Berglund et al. |
| 4,323,557 | A | 4/1982 | Rosso et al. |
| 4,476,293 | A | 10/1984 | Robinson |
| 4,499,896 | A | 2/1985 | Heinecke |
| 4,563,388 | A | 1/1986 | Bonk et al. |
| 4,584,192 | A | 4/1986 | Dell et al. |
| 4,643,180 | A | 2/1987 | Feld et al. |
| 4,666,896 | A | 5/1987 | Warner et al. |
| 4,798,201 | A | 1/1989 | Rawlings et al. |
| 4,999,210 | A | 3/1991 | Solomon et al. |
| 5,013,306 | A | 5/1991 | Solomon et al. |
| 5,015,228 | A | 5/1991 | Columbus et al. |
| 5,017,625 | A | 5/1991 | Ansell |
| 5,019,096 | A * | 5/1991 | Fox, Jr. ............... A61B 42/10 2/167 |
| 5,045,601 | A | 9/1991 | Capelli et al. |
| 5,069,907 | A | 12/1991 | Mixon et al. |
| 5,089,205 | A * | 2/1992 | Huang ............... A61L 31/049 2/168 |
| 5,165,952 | A | 11/1992 | Solomon et al. |
| 5,183,664 | A | 2/1993 | Ansell |
| 5,290,615 | A | 3/1994 | Tushaus et al. |
| 5,369,155 | A | 11/1994 | Asmus |
| 5,382,451 | A | 1/1995 | Johnson et al. |
| 5,389,093 | A | 2/1995 | Howell |
| 5,616,338 | A | 4/1997 | Fox et al. |
| 5,645,855 | A | 7/1997 | Lorenz |
| 5,686,096 | A | 11/1997 | Khan et al. |
| 5,690,958 | A | 11/1997 | McGrath |
| 5,707,366 | A | 1/1998 | Solomon et al. |
| 5,717,005 | A * | 2/1998 | Richardson ............ A61L 15/46 424/448 |
| 5,763,412 | A | 6/1998 | Khan et al. |
| 5,803,086 | A * | 9/1998 | Scholz ............... A61B 46/00 128/849 |
| 5,985,395 | A | 11/1999 | Comstock et al. |
| 6,106,505 | A | 8/2000 | Modak et al. |
| 6,132,765 | A | 10/2000 | DiCosmo et al. |
| 6,139,856 | A | 10/2000 | Kaminska et al. |
| 6,224,579 | B1 | 5/2001 | Modak et al. |
| 6,228,393 | B1 | 5/2001 | DiCosmo et al. |
| 6,461,467 | B2 | 10/2002 | Blatchford et al. |
| 6,475,516 | B2 | 11/2002 | DiCosmo et al. |
| 6,488,948 | B1 | 12/2002 | Danieli |
| 6,500,466 | B2 | 12/2002 | Werle et al. |
| 6,582,719 | B2 | 6/2003 | Modak et al. |
| 6,607,746 | B2 | 8/2003 | Cox et al. |
| 6,742,522 | B1 * | 6/2004 | Baker ............... A61B 46/10 128/849 |
| 6,808,738 | B2 | 10/2004 | DiTizio et al. |
| 6,838,078 | B2 | 1/2005 | Wang et al. |
| 6,843,784 | B2 | 1/2005 | Modak et al. |
| 6,872,195 | B2 | 3/2005 | Modak et al. |
| 6,939,554 | B2 | 9/2005 | McDonald et al. |
| 7,066,916 | B2 | 6/2006 | Keaty et al. |
| 7,189,793 | B2 | 3/2007 | Wang et al. |
| 7,297,143 | B2 | 11/2007 | Woloszko et al. |
| 7,323,163 | B2 | 1/2008 | Wang et al. |
| 7,329,412 | B2 | 2/2008 | Modak et al. |
| 7,427,574 | B2 | 9/2008 | Allen |
| 7,488,757 | B2 | 2/2009 | Hoang |
| 7,537,779 | B2 | 5/2009 | Modak et al. |
| 7,771,743 | B1 | 8/2010 | Luthra et al. |
| 7,999,023 | B2 | 8/2011 | Menon et al. |
| 8,026,407 | B2 | 9/2011 | Downs et al. |
| 8,354,123 | B2 | 1/2013 | DiTizio et al. |
| 8,361,501 | B2 | 1/2013 | DiTizio et al. |
| 8,383,143 | B2 | 2/2013 | Modak et al. |
| 8,481,138 | B2 | 7/2013 | Miller et al. |
| 8,591,493 | B2 | 11/2013 | McGuire, Jr. |
| 9,028,852 | B2 | 5/2015 | Scholz |
| 2001/0055511 | A1 | 12/2001 | Baumann et al. |
| 2002/0051812 | A1 | 5/2002 | DiCosmo et al. |
| 2003/0224033 | A1 | 12/2003 | Li et al. |
| 2004/0086568 | A1 | 5/2004 | DiTizio et al. |
| 2004/0126355 | A1 | 7/2004 | Childers |
| 2004/0137065 | A1 | 7/2004 | Vogt et al. |
| 2005/0137375 | A1 | 6/2005 | Hansen et al. |
| 2005/0158252 | A1 * | 7/2005 | Romanowski ......... A61K 8/345 424/49 |
| 2007/0009580 | A1 | 1/2007 | DiCosmo et al. |
| 2007/0212419 | A1 | 9/2007 | Bako et al. |
| 2008/0026015 | A1 | 1/2008 | MacDonald et al. |
| 2008/0026025 | A1 * | 1/2008 | Gooch ................ A01N 47/44 424/405 |
| 2008/0060550 | A1 | 3/2008 | MacDonald et al. |
| 2008/0063615 | A1 | 3/2008 | MacDonald et al. |
| 2008/0078413 | A1 | 4/2008 | Padget et al. |
| 2008/0142023 | A1 * | 6/2008 | Schmid ................ A01N 25/10 128/849 |
| 2009/0035388 | A1 | 2/2009 | Dudnyk et al. |
| 2009/0098073 | A1 | 4/2009 | MacDonald et al. |
| 2009/0098081 | A1 | 4/2009 | MacDonald et al. |
| 2009/0123569 | A1 | 5/2009 | MacDonald et al. |
| 2009/0155197 | A1 | 6/2009 | Smith et al. |
| 2010/0022654 | A1 | 1/2010 | Asmus et al. |
| 2010/0069854 | A1 | 3/2010 | Okoh et al. |
| 2010/0087788 | A1 | 4/2010 | Rosenblatt et al. |
| 2010/0234815 | A1 | 9/2010 | Do et al. |
| 2010/0282409 | A1 | 11/2010 | Hobbs et al. |
| 2011/0100293 | A1 | 5/2011 | Abbasian et al. |
| 2011/0100294 | A1 | 5/2011 | Abbasian et al. |
| 2011/0104390 | A1 | 5/2011 | Abbasian et al. |
| 2011/0137006 | A1 | 6/2011 | McGuire et al. |
| 2011/0212152 | A1 | 9/2011 | DiTizio et al. |
| 2011/0241261 | A1 | 10/2011 | McGuire et al. |
| 2011/0256185 | A1 | 10/2011 | Yang et al. |
| 2011/0313048 | A1 | 12/2011 | Yang et al. |
| 2012/0330210 | A1 | 12/2012 | Yang et al. |
| 2013/0039953 | A1 | 2/2013 | Dudnyk et al. |
| 2013/0065965 | A1 | 3/2013 | Salguero et al. |
| 2013/0239977 | A1 | 9/2013 | McGuire, Jr. et al. |
| 2013/0303656 | A1 | 11/2013 | Wibaux et al. |
| 2015/0165097 | A1 | 6/2015 | Parthasarathy et al. |
| 2015/0238444 | A1 | 8/2015 | Menon et al. |
| 2015/0322229 | A1 | 11/2015 | Bui et al. |
| 2015/0328360 | A1 | 11/2015 | Menon et al. |
| 2016/0001058 | A1 | 1/2016 | Ziebol et al. |
| 2016/0050934 | A1 | 2/2016 | McGuire, Jr. |
| 2016/0081894 | A1 | 3/2016 | Hoang et al. |

FOREIGN PATENT DOCUMENTS

| | | |
|---|---|---|
| EP | 0379269 | 3/1994 |
| EP | 2229964 | 9/2010 |
| EP | 2229964 A1 | 9/2010 |
| GB | 2349644 A | 11/2000 |
| WO | WO 90/00066 | 1/1990 |
| WO | WO 93/02717 | 2/1993 |
| WO | WO 98/51352 | 11/1998 |
| WO | WO-00/57933 | 10/2000 |
| WO | WO-02/51464 | 7/2002 |

(56) References Cited

FOREIGN PATENT DOCUMENTS

| WO | WO-03/066721 A1 | 8/2003 |
|---|---|---|
| WO | WO-2007/132239 | 11/2007 |
| WO | WO-2009/015476 | 2/2009 |
| WO | WO-2011/061272 | 5/2011 |
| WO | WO-2011/061272 A1 | 5/2011 |
| WO | WO-2011/156910 | 12/2011 |
| WO | WO-2014/124232 | 8/2014 |

OTHER PUBLICATIONS

"3M Incise Drapes," *3M Technical Brochure*, (3M Company, St. Paul, MN), (Jan. 1, 2001).
"3M Incise Drapes: Bibliography of Efficacy and Safety Studies," *3M Technical Brochure*, (3M Company, St. Paul, MN), (Jan. 1, 2002).
"3M Tegaderm CHG Chlorhexidine Gluconate IV Securement Dressing," *3M Technical Brochure*, (3M Company, St. Paul, MN), (Jan. 1, 2007).
"Antimicrobial Susceptibility Test: Zone of Inhibition," *Doc. No. STP0124*, (Nelson Laboratories, Inc., Salt Lake City, UT), (Jan. 1, 2006).
"Cesarean/Abdominal Fluid Collection Drape With Fenestration, 100 in.×72 in.×120 in., Sterile," http://nacrm.kcmkt.com/scripts/wgate/zkcnab2c/!?p_shop=ZKCHCSHOP, (Jan. 9, 2009).
"MCD—Disposable Surgical Drapes Cross Reference," http://www.medconceptsdev.com/products_D_Xreference.htm, (Jan. 9, 2009).
"MCD—Surgical Drapes," http://www.medconceptsdev.com/Catalog_template.asp?top=acti-gard&cid=99, (Jan. 9, 2009).
Karpanen, TJ et al., "Penetration of Chlorhexidine into Human Skin," *Antimicrob Agents Chemother*., Oct. 2008;52(10):3633-6.
Moureau, Nancy L., et al., "Evaluation of the Clinical Performance of a Chlorhexidine Gluconate Antimicrobial Transparent Dressing," *Journal of Infection Prevention*, 2009; vol. 10, Supp. 1 http://bji.sagepub.com/cgi/content/abstract/10/1_suppl/s13, (Sep. 30, 2009).
"3M DuraPrep Surgical Solution (Iodine Povacrylex [0.7% available Iodine] and Isopropyl Alcohol, 74% w/w) Patient Preoperative Skin Preparation," http://solutions.3m.com/wps/portal/3M/en_US/infection-prevention-solutions/home/products/?PC_7_RJH9U52308DUB0IIL8TMGN3013000000_nid=GSF83Z3YYXbeFM2XGMRS15gl.
"3M DuraPrep Surgical Solution Drug Label," http://dailymed.nlm.nih.gov/dailymed/drugInfo.cfm?id=38755.
"ChloraPrep 26mL Applicator," CareFusion Corporation (2011).
"ChloraPrep One-Step—chlorhexidine gluconate and isopropyl alcohol solution—Drug Label," http://nccs-dailymed.nlm.nih.gov/dailymed/archives/fdaDrugInfo.cfm?archiveid=11471 (Nov. 9, 2011).
"The Power of Povacrylex," 3M Company (Dec. 31, 2009).
Groesbeck, Michael L., "Cardinal Health Letter to Food and Drug Administration Re ANDA for Preoperative Prep with Tint" (Nov. 18, 2004).
Hamilton, Chris, "ChloraPrep Pros & Cons," http://www.ehow.com/list_6884562_chloraprep-pros-_amp_amp_-cons.html (Nov. 9, 2011).
"Dow Corning Soft Skin Adhesives Parts A & B," *Dow Corning Product Information*, Ref. No. 52-1128-01 (Jul. 31, 2009).
"SurgiClear Antimicrobial Clear Silicone Adhesive Dressing with Chlorhexidine and Silver," www.covalon.com; Covalon Technologies Ltd.
Basrani, Bettina R., et al., "Using Diazotization to Characterize the Effect of Heat or Sodium Hypochlorite on 2.0% Chlorhexidine," *Jour. of Endodont.*, vol. 35, No. 9 (Sep. 2009) pp. 1296-1299.
Boehncke, A. et al., "4-Chloroaniline," *Concise International Chemical Assessment Document 48*, World Health Organization, ISBN 92 4 153048 0 (2003).
Cropper, E. et al., "Analytical Procedures for the Determination of Chlorhexidine in Oral Products," *J. Soc. Cosmet.*, vol. 26 (1975) pp. 355-373.
DiTizio, Val et al., "Dual Antimicrobial Silicone Adhesive Dressings. A White Paper. What's the Difference, and Why It Matters.," www.covalon.com; Covalon Technologies Ltd. (2013).
Joseph, Siji, "Quantification of 4-Chloroaniline in Chlorhexidine Using the Agilent 1200 Series Rapid Resolution LC System Coupled with the Agilent 6410B Triple Quadrupole LC/MS System," Agilent Technologies, Inc., Publication No. 5990-3676EN (Mar. 15, 2009).
Nicolay, Alain et al., "Rapid HPLC Method for Determination of Parachloroaniline in Chlorhexidine Antiseptic Agent in Mouthrinses, Ophthalmic and Skin Solution," *American Journal of Analytical Chemistry*, vol. 2 (Aug. 31, 2011) pp. 422-428.
Ranganathan, N. S., "Chlorhexidine," *Handbook of Antiseptics and Disinfectants*, Marcel Dekker, Inc. (New York), Joseph Ascenzi (ed.) (1996) pp. 236-237.
Zong, Zhixin et al., "Studies on the Instability of Chlorhexidine, Part I: Kinetics and Mechanisms," *Journal of Pharmaceutical Sciences*, vol. 101, No. 7 (Jul. 2012) pp. 2417-2427.
"Dow Aculyn 22," (Sep. 2002) pp. 1-12.
Hemani, Micah L. et al., "Skin Preparation for the Prevention of Surgical Site Infection: Which Agent is Best?", *Reviews in Urology*, vol. 11, No. 4 (2009) pp. 190-195.
"Topical Antimicrobials in the Control of Wound Bioburden—Part 2," *Ostomy Wound Management*, vol. 52, Issue 8 (Aug. 2006) pp. 1-10.
Decker, C., "The Use of UV Irradiation in Polymerization," *Polym. Int.*, 45:133-141 (Mar. 26, 1999).
Kohlbecker, G., "Toxic Impurities in Chlorhexidine Digluconate," *Deutsche Zahnarztliche Zeitschrift*, 44(4):273-276, (1989) [Abstract].
Tallury, Padmavathy et al., "Poly(ethylene-co-vinyl acetate) Copolymer Matrix for Delivery of Chlorhexidine and Acyclovir Drugs for Use in the Oral Environment: Effect of Drug Combination, Copolymer Composition and Coating on the Drug Release Rate," *Dent Mater*., 23(4):404-9. (Apr. 2007) [Epub Mar. 23, 2006].
Ward, J. H., et al., "Micropatterning of Biomedical Polymer Surfaces by Novel UV Polymerization Techniques," *J. Biomed. Mater. Res.*, 56:351-360 (Apr. 24, 2001).

* cited by examiner

CHLORHEXIDINE-CONTAINING ANTIMICROBIAL LAMINATES

CROSS-REFERENCE TO RELATED APPLICATIONS

This application is a U.S. National Stage of PCT Patent Application No. PCT/US10/20402, filed on Jan. 7, 2010, which claims the benefit of U.S. Provisional Patent Application No. 61/142,896, filed on Jan. 7, 2009.

BACKGROUND OF THE INVENTION

The present invention relates generally to antimicrobial laminates, such as surgical drapes, employing chlorhexidine.

Many types of surgical drapes are known. Some include an adhesive layer for adhering the surgical drape to a patient's skin or other surface. One such drape is an incise drape. An "incise drape" is one where a surgical incision is made directly through the drape and into a patient. By definition, a skin surface covered by a sterile incise drape is bacteria-free (i.e., sterilized) at the beginning of a surgical procedure. Ideally, the skin surface remains bacteria-free during the procedure, resisting the transfer of bacteria from, for example, gloves, instruments, and sponges that may come in contact with not only the surgical wound but also the surrounding skin. A drape's barrier and antimicrobial properties are typically effective only so long as the drape is securely attached to the skin.

Adhesion of a drape to skin can be affected by a wide variety of considerations, including the type of any skin prepping solution applied to the skin before the drape is adhered thereto. For example, a 2007 technical brochure published by 3M Company (St. Paul, Minn.) describes test results illustrating that 3M's DuraPrep Surgical Solution (an iodine povacrylex and isopropyl alcohol solution available from 3M Company of St. Paul, Minn.) facilitates better adhesion of drapes to skin prepped therewith as compared to skin prepped with ChloraPrep (a solution containing 2% chlorhexidine gluconate in 70% isopropyl alcohol available from Cardinal Health, Inc. through its Enturia Division in Leawood, Kans.).

In contrast to surfaces covered by a sterile incise drape, a skin surface that has been "prepped" has only been disinfected, not sterilized. It is known that prepping a skin surface does not always completely eradicate bacteria. Even after prepping, bacteria regeneration continuously occurs on a skin surface. Further, skin prepping solutions are vulnerable to removal or neutralization by blood, irrigation fluids, exudates, and the like, which are commonly associated with surgical procedures.

A variety of surgical incise drapes are known, but adequate adhesion of such drapes to skin is of ongoing concern. Conventional surgical incise drapes contain at least one skin-compatible adhesive coated on a backing. While many different chemistries have been contemplated for use in backings within surgical incise drapes, geometry of those backings is generally more limited. Conventional surgical drape backings are generally at least 1.5 mils (40 microns) thick. Such backings are conventionally used to impart, among other properties, structural integrity to the drape.

While the use of thinner backings is contemplated in certain configurations, those configurations are limited and specific. For example, U.S. Pat. No. 5,803,086 describes a film backing for surgical incise drapes as generally having a thickness of less than 200 microns (7.87 mils) and preferably about 6 to 130 microns (0.24 mil to 5.12 mils). The drapes therein are linerless.

Further, U.S. Pat. No. 5,183,664 describes a configuration where a hydrophilic polyurethane gel adhesive layer is interfaced with a backing. The adhesive layer may contain an antibacterial agent, including chlorhexidine and salts thereof. A backing layer having a thickness of as low as 10 microns (0.39 mil) is described in this configuration. In such a configuration, however, the backing does not provide structural integrity, but merely functions as an outwardly exposed barrier layer. The adhesive layer has a thickness of 10 microns (0.39 mil) to 100 microns (3.94 mils), preferably 35 microns (1.38 mils) to 45 microns (1.77 mils), when used in conjunction with nonexuding wounds. However, the adhesive layer is stated to have a thickness of 0.5 mm (19.69 mils) to 5 mm (196.85 mils), preferably 2 mm (78.74 mils) to 3 mm (118.11 mils), when used in conjunction with exuding wounds. The use of substantially thicker adhesive layers as compared to those traditionally used in incise drapes and dressings is described as being driven by the desire to take advantage of the absorptive properties of the material forming the adhesive layer. Generally, however, the thicker the backing and other layer(s) of materials within a surgical incise drape, the more difficult it tends to be for such drapes to conform to a patient's skin surface and stay adequately adhered to that skin surface. For example, when performing an incision through such a drape, force from frictional drag of a scalpel used to make such an incision can cause lifting of the incise drape's edge during use. Further, when drapes are used to cover areas on a patient's skin that undergo significant movement during the surgical procedure (e.g., when drapes are placed proximate a knee joint being replaced, during which procedure the replacement knee joint must be extensively manipulated after its implant to ensure proper range of motion and fit), lifting of the incise drape from the skin surface is more likely.

Adding to the challenge of adequate adherence of a surgical incise drape to skin is compatibility of the adhesive with not only the skin but also any antimicrobial agents incorporated therein. Select antimicrobial agents have been incorporated into skin-compatible adhesives.

For example, U.S. Pat. No. 4,323,557, assigned on its face to 3M Company, describes a pressure-sensitive adhesive containing iodine. 3M Company markets an iodine-containing surgical drape under the IOBAN trade designation. 3M IOBAN 2 Antimicrobial Incise Drapes, available from 3M Company of St. Paul, Minn., are stated to be useful in reducing the risk of wound contamination and bacterial migration. 3M IOBAN 2 Antimicrobial Incise Drapes—6661 EZ, also available from 3M Company of St. Paul, Minn., are stated to be specifically adapted for minimally invasive surgical procedures using implantable devices and/or materials. According to 3M Company's technical literature, an iodophor-impregnated adhesive on such incise drapes is stated to provide continuous, broad-spectrum antimicrobial activity and superior adhesion to the skin and wound edge. See also U.S. Pat. No. 7,189,793, assigned on its face to 3M Innovative Properties Company, which discloses an iodine/iodide-containing hot melt coatable adhesive used in surgical drapes.

Iodine, however, has not proven to be as effective as desired in halting the spread of bacteria promoting staphylococcal infections. Staphylococcal (i.e., "staph") infections are communicable infections caused by staph organisms, and they are often characterized by the formation of abscesses. They are said to be the leading cause of primary infections originating in hospitals in the United States.

Classified since the early twentieth century as among the deadliest of all disease-causing organisms, staph exists on the skin or inside the nostrils of 20-30% of healthy people. It is sometimes found in breast tissue, the mouth, and the genital, urinary, and upper respiratory tracts. Although staph bacteria are usually harmless, when injury or a break in the skin enables the organisms to invade the body and overcome the body's natural defenses, consequences can range from minor discomfort to death. Infection is most apt to occur in the following classes of people: newborns (especially those born prematurely); women who are breast-feeding; individuals whose immune systems have been undermined by radiation treatments, chemotherapy, HIV, or medication; intravenous drug users; and those with surgical incisions, skin disorders, and serious illnesses like cancer, diabetes, and lung disease. Risk of infection is greatest among the very young and the very old.

The United States' Center for Disease Control (CDC) recommends chlorhexidine gluconate as the preferred skin antiseptic over tinctures of iodine, iodophors, and alcohol. Chlorhexidine gluconate, however, is a cationic molecule that is known to become inactive over time if exposed to anionic materials on, for example, skin. Nevertheless, chlorhexidine gluconate has been recently introduced by 3M Company (St. Paul, Minn.) into dressings used, for example, in dressing catheter insertion sites. 3M Company's TEGADERM CHG (Chlorhexidine Gluconate) IV Securement Dressing is stated to provide the antimicrobial properties of chlorhexidine gluconate with the simplicity, reliability, and dependability of 3M's TEGADERM dressings. In order to extend the typically short antimicrobial life of chlorhexidine gluconate within the dressing, 3M Company's technical literature describes how the chlorhexidine gluconate is dissolved into a soft gel pad to provide a reservoir of antiseptic for consistent and continuous coverage over time. The same latex-free adhesive is used to secure 3M Company's TEGADERM CHG IV Securement Dressing to skin as is used in 3M Company's non-CHG TEGADERM dressing. See also U.S. Pat. No. 6,461,467, assigned on its face to 3M Innovative Properties Company, which describes the use of an antimicrobial adhesive containing chlorhexidine gluconate with 3M Company's TEGADERM dressings.

Chlorhexidine, a substituted diguanide, has a high degree of antimicrobial activity, low mammalian toxicity, and the ability to bind to the stratum corneum layer of skin and to mucous membranes. The bactericidal activity of chlorhexidine is much greater than that of monomeric biguanides. These unique characteristics make it particularly attractive as an active ingredient in antimicrobial skin preparations.

Besides its use in specific medical dressings and skin antiseptics, the efficacy of chlorhexidine in providing antimicrobial protection is known further throughout the medical industry. For example, U.S. Pat. No. 7,329,412 describes an antimicrobial catheter prepared by treating a polymeric catheter with a solution comprising a solvent and an antimicrobial mixture consisting essentially of chlorhexidine free base and a water-soluble chlorhexidine salt, wherein the weight ratio of chlorhexidine free base to water-soluble chlorhexidine salt in the solution is between 1:1 to 1:5. As background therein, duration of the antimicrobial efficacy of medical devices impregnated with chlorhexidine salts, such as chlorhexidine acetate, is discussed as being short lived. Further discussed is the fact that chlorhexidine free base is not generally known to be soluble in water or alcohol, which generally prevents it from being impregnated in sufficient amounts because of low solubility in a solvent system. Thus, the combination of chlorhexidine free base and a water-soluble chlorhexidine salt, at the particular ratios described therein, was found to provide improved antimicrobial effectiveness through an increased uptake of chlorhexidine into, increased retention of chlorhexidine in, and prolonged release of chlorhexidine from the medical device, while utilizing relatively low levels of chlorhexidine.

U.S. Pat. No. 5,165,952 relates to medical articles employing chlorhexidine. When bulk-distributed in a medical article, chlorhexidine is described as being known to adversely affect certain characteristics of the article, such as tensile strength; and, when the medical article is formed of a plastic material, high temperatures often needed for extension of such plastic materials into the form of a medical article are described as potentially damaging the chlorhexidine within. Thus, chlorhexidine is both coated on and bulk-distributed throughout the medical articles according to the disclosure therein. Similarly, U.S. Pat. No. 5,089,205 relates to incorporation of chlorhexidine free base or one of its salts into a medical device such as a glove. The chlorhexidine can be incorporated by both distribution and dipping processes.

Chlorhexidine, in its pure form and in its salt forms, is also discussed as being useful as a preservative and as an antimicrobial in compositions for oral hygiene. See, for example, U.S. Patent Publication No. 20050158252.

U.S. Patent Publication No. 20080026025 also discusses the use of chlorhexidine, specifically in water purification applications. As discussed therein, chlorhexidine is a 1,6-di (4-chlorophenyl-diguanido) hexane having the chemical formula:

Chlorhexidine is discussed therein as having a high level of antibacterial activity, low mammalian toxicity, and a strong affinity for binding to skin and mucous membranes.

Also discussed in U.S. Patent Publication No. 20080026025 is the history of using chlorhexidine only in its salt soluble forms. Chlorhexidine salts are stated to have an extremely bitter taste that must be masked in formulations intended for oral use. In addition, chlorhexidine salts are stated to be ineffective for applications requiring insoluble materials. As such, preparation and use of chlorhexidine dihydrate in accordance with the disclosure therein was found to provide advantages over known chlorhexidine-containing compositions.

Chlorhexidine dihydrate is described in U.S. Patent Publication No. 20080026025 as being amorphous in structure as opposed to the 100% crystalline structure of pure chlorhexidine. Chlorhexidine dihydrate is also described as disrupting microorganisms in a principally surface-dependent manner, advantageously without depleting the supply of the chlorhexidine dehydrate (i.e., the antimicrobial functionality is effectively catalytic). Such treatment, being a zero-order reaction, was found capable of proceeding without consumption of any chlorhexidine dihydrate. In contrast, the rate of reaction for pure chlorhexidine and its previously known conventional derivatives is described therein as being second-order, as those reactions depend on both the concentration of chlorhexidine and the active sites of microorganisms. In such conventional reactions, chlorhexidine is described as being consumed during the reaction.

Nevertheless, improved antimicrobial laminates, such as surgical drapes, are desired. For example, improvements with respect to a surgical drape's or other medical dressing's adhesion to a variety of skin surfaces and its role in halting the spread of bacteria promoting staphylococcal infections are needed.

BRIEF SUMMARY OF THE INVENTION

Antimicrobial laminates of the invention comprise at least one adhesive layer; a backing outwardly exposed on a first side of the adhesive layer; and, optionally, a release liner outwardly exposed on a second side of the adhesive layer opposite from the first side of the adhesive layer. At least one of the at least one adhesive layer and the backing comprises an antimicrobially effective amount of substantially pure chlorhexidine. According to an exemplary embodiment, the antimicrobial laminate is a surgical incise drape.

According to one embodiment, the at least one adhesive layer is essentially free of antimicrobial agents. According to another embodiment, the backing is essentially free of antimicrobial agents. According to a further embodiment, the laminate is essentially free of chlorhexidine salt.

In one embodiment, the at least one adhesive layer comprises the antimicrobially effective amount of the substantially pure chlorhexidine. In an exemplary embodiment, the at least one adhesive layer comprises at least about 3% by weight of the substantially pure chlorhexidine. In a further exemplary embodiment, the at least one adhesive layer comprises about 8.75% by weight of the substantially pure chlorhexidine.

According to one aspect of the invention, the laminate essentially comprises substantially transparent or translucent flexible polymeric materials. According to another aspect of the invention, the backing comprises a polyurethane base polymer. According to yet another aspect of the invention, the at least one adhesive layer comprises a (meth)acrylate adhesive.

According to one aspect of the invention, the backing, irrespective of any structural integrity provided by the at least one adhesive layer, imparts structural integrity to the laminate. In preferred embodiments, the backing is extensible. In one embodiment, the backing has a thickness of about 14 microns or less. According to a further embodiment, the backing has a thickness of about 6 microns or less.

In one embodiment, the at least one adhesive layer has a thickness of about 5 microns to about 150 microns. In a further embodiment, the at least one adhesive layer has a thickness of about 30 microns to about 100 microns. In yet a further embodiment, the at least one adhesive layer has a thickness of about 10 microns to about 50 microns.

In one embodiment, the at least one adhesive layer comprises a pressure-sensitive adhesive. In another embodiment, the at least one adhesive layer comprises a skin-compatible adhesive. According to one aspect of the invention, when the laminate is tested against stainless steel according to ASTM D1000, the laminate has an adhesion level of at least about 350 mL/cm. According to further aspect of the invention, when the laminate is tested against stainless steel according to ASTM D1000, the laminate has an adhesion level of at least about 580 mL/cm.

DETAILED DESCRIPTION OF THE INVENTION

Figure 1:
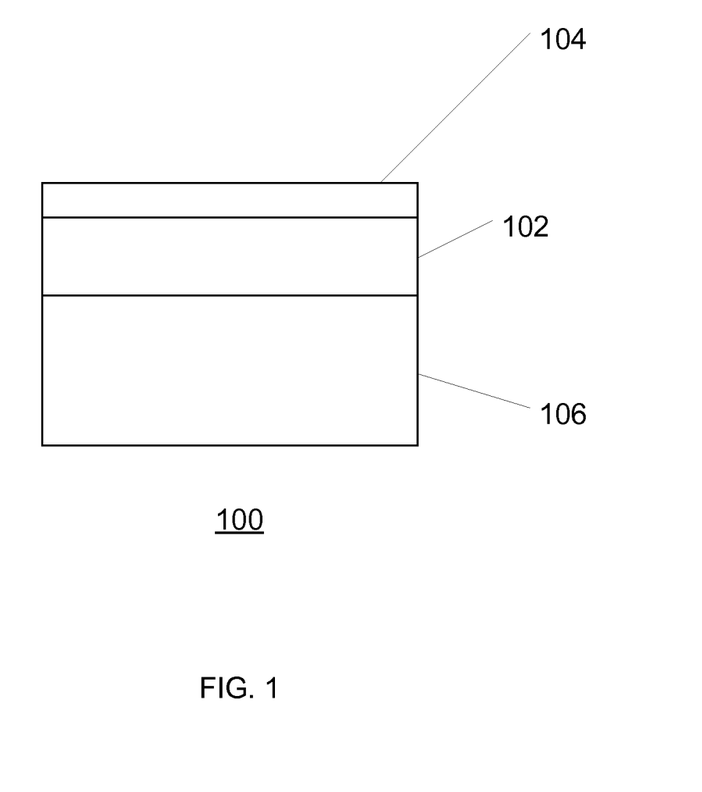
FIG. 1 is a schematic cross-sectional representation of a portion of an antimicrobial laminate according to the invention.

According to the invention, and as illustrated in FIG. 1, an antimicrobial laminate 100, such as a surgical drape, comprises an adhesive 102 adjacent a backing 104. Until its application to a surface, a release liner 106 can be positioned on the adhesive 102 opposite the backing 104.

When the antimicrobial laminate is used as a surgical incise drape, preferably the surgical drape is formed from substantially transparent or translucent flexible polymeric materials. The resulting drape's transparency or translucency facilitates precise placement of the drape on a patient's skin surface, but also precise placement of an incision therethrough. Preferably, the drape also allows for moisture evaporation therethrough as desired, especially during prolonged surgeries.

Backings of the invention have a thickness of about 0.55 mil (14 microns) or less. In one preferred embodiment, a backing for an antimicrobial laminate has a thickness of about 0.24 mil (6 microns) or less. Preferably, the backing, irrespective of any structural integrity provided by the adhesive layer, imparts structural integrity to the drape. Structural integrity is evidenced by, for example, elongation properties with minimal deformation as discussed below. In preferred embodiments, when antimicrobial laminates are removed from a substrate, the adhesive is capable of debonding from the substrate by microfracturing along the bond line without separation between layers within the laminate. In further preferred embodiments, the backing is advantageously not only capable of imparting structural integrity, but it is also extensible to enable ease of application and adequate adherence of the antimicrobial laminate to non-planar surfaces.

The terms "extensible" and "extensibility" refer to a material's ductility and its ability to be stretched and recover to essentially its original state after stretching. Extensible backings are capable of recovering to their original state when stretched (i.e., elongated) up to about 125% of their initial length or more. Preferably, extensible backings are capable of recovering to their original state when stretched up to about 150% of their initial length or more. According to one aspect of the invention, extensible backings are capable of elongating more than 200% before breaking. Further preferable are extensible backings that exhibit essentially no plastic deformation when stretched up to about 150% of their initial length.

According to one aspect of the invention, extensible backings of the invention exhibit greater than about 210% elongation at break when tested according to the Tensile Testing Method described below. In a further embodiment, extensible backings of the invention exhibit greater than about 260% elongation at break when tested according to the Tensile Testing Method described below. In a still further embodiment, extensible backings of the invention exhibit greater than about 300% elongation at break when tested according to the Tensile Testing Method described below. In a further embodiment still, extensible backings of the invention exhibit greater than about 350% elongation at break when tested according to the Tensile Testing Method described below.

"Tensile Testing Method": For tensile testing, samples of the backing material can be formed into standard tensile testing specimens according to ASTM D638-95 using designations for Type II measurements. Tensile testing is then performed according to ASTM D638-95. The rate at which the jaws holding the specimen are pulled in a tensile manner is set at 300 millimeters/minute (11.8 inches/minute) to obtain the percent elongation at break.

According to another aspect of the invention, extensible backings of the invention exhibit less than about 3% deformation after 25% elongation when tested according to the Recovery Testing Method described below. In a further embodiment, extensible backings of the invention exhibit less than about 2% deformation after 25% elongation when tested according to the Recovery Testing Method described below. In a still further embodiment, extensible backings of the invention exhibit less than about 1% deformation after 25% elongation when tested according to the Recovery Testing Method described below.

According to another aspect of the invention, extensible backings of the invention exhibit less than about 8% deformation after 50% elongation when tested according to the Recovery Testing Method described below. In a further embodiment, extensible backings of the invention exhibit less than about 5% deformation after 50% elongation when tested according to the Recovery Testing Method described below. In a still further embodiment, extensible backings of the invention exhibit less than about 2% deformation after 50% elongation when tested according to the Recovery Testing Method described below.

"Recovery Testing Method": For recovery testing, a generally rectangular sample of the backing material having an initial length of 25 centimeters (10 inches) and width of 5 centimeters (2 inches) can be prepared. The sample is then stretched in tension until its length exceeds its initial length by a predetermined percentage (25% or 50%). After recovery equilibrium is obtained (approximately 5-10 minutes), the length of the relaxed sample is measured and the sample can be qualitatively analyzed for defects or deformation. The change in length of the sample as compared to the initial length is its % deformation.

According to another aspect of the invention, extensible backings of the invention require a force of less than about 40 Newtons to elongate the backing to 150% its initial length. In a further embodiment, extensible backings of the invention require a force of less than about 30 Newtons to elongate the backing to 150% its initial length. In yet a further embodiment, extensible backings of the invention require a force of less than about 20 Newtons to elongate the backing to 150% its initial length.

In order to determine the force required to elongate a backing material to 150% of its initial length, a generally rectangular sample having an initial length of 12.5 centimeters (5 inches) and width of 5 centimeters (2 inches) can be measured using an IMASS SP2000 slip/peel tester (available from IMASS, Inc. of Accord, Mass.) operating at a speed of 30 centimeters/minute (12 inches/minute).

The backing of antimicrobial laminates of the invention comprises any suitable material. Suitable chemistries for the backing comprise polyolefins (e.g., low density polyethylene), polyurethanes (e.g., polyester polyurethane or polyether polyurethane), polyesters (e.g., polyether polyester), and polyamides (e.g., polyether polyamide). In an exemplary embodiment, the backing comprises a base polymer selected from a polycarbonate, a polyvinyl fluoride, a poly(meth)acrylate (e.g., a polyacrylate or a polymethacrylate), a polyurethane, modified (e.g., hybrid) polymers thereof, or combinations thereof.

Preferably, the base polymer is of relatively high molecular weight. That is, while the backing can be formed by extrusion according to some embodiments of the invention, the material comprising a base polymer of the backing is preferably of a sufficient molecular weight that extrusion thereof is not practical (i.e., if a polyurethane, the polyurethane is not considered extrusion-grade polyurethane by those of ordinary skill in the art).

In one embodiment, the backing comprises a polyurethane base polymer. For simplicity, the term "polyurethane" as used herein includes polymers containing urethane (also known as carbamate) linkages, urea linkages, or combinations thereof (i.e., in the case of poly(urethane-urea) s). Thus, polyurethanes of the invention contain at least urethane linkages and, optionally, urea linkages. In one embodiment, polyurethanes of the invention comprise a backbone having at least about 80% urethane and/or urea repeat linkages formed during their polymerization.

Polyurethane chemistry is well known to those of ordinary skill in the art. Polyurethane based polymers according to the invention can contain polyurethane polymers of the same or different chemistries, the latter commonly understood to be a polymer blend. Polyurethanes generally comprise the reaction product of at least one isocyanate-reactive component, at least one isocyanate-functional component, and one or more other optional components such as emulsifiers and chain extending agents.

As a backing, a polyurethane film can be prepared and formed into a film using solution or dispersion chemistry and film coating techniques known to those skilled in the art. According to one aspect of the invention, a backing of the desired thickness is formed using dispersion chemistry. Dispersion chemistry is well known to those skilled in the art. While the % solids will vary, in one embodiment, a dispersion having about 10-15% solids was found useful for formation of the backing.

First, components, including at least one isocyanate-reactive component, at least one isocyanate-functional component, and, optionally, at least one reactive emulsifying compound, are reacted to form an isocyanate-terminated polyurethane prepolymer. The polyurethane prepolymer can then be dispersed, and optionally chain-extended, in a dispersing medium to form a polyurethane-based dispersion that can be cast to form a polyurethane film.

When the polyurethane film is prepared from an organic solventborne or waterborne system, once the solution or dispersion is formed, it is easily applied to a substrate and then dried to form a polyurethane film. As known to those of ordinary skill in the art, drying can be carried out either at room temperature (i.e., about 20° C.) or at elevated temperatures (e.g., about 25° C. to about 150° C.). For example, drying can optionally include using forced air or a vacuum. This includes the drying of static-coated substrates in ovens, such as forced air and vacuum ovens, or drying of coated substrates that are continuously conveyed through chambers heated by forced air, high-intensity lamps, and the like. Drying may also be performed at reduced (i.e., less than ambient) pressure.

Any suitable isocyanate-reactive component can be used in this embodiment of the present invention. The isocyanate-reactive component contains at least one isocyanate-reactive material or mixtures thereof. As understood by one of ordinary skill in the art, an isocyanate-reactive material includes at least one active hydrogen. Those of ordinary skill in the polyurethane chemistry art will understand that a wide variety of materials are suitable for this component. For example, amines, thiols, and polyols are isocyanate-reactive materials.

However, it is preferred that the isocyanate-reactive material be a hydroxy-functional material. Polyols are the preferred hydroxy-functional material used in the present invention. Polyols provide urethane linkages when reacted with an isocyanate-functional component, such as a polyisocyanate.

Polyols, as opposed to monols, have at least two hydroxy-functional groups. Diols contribute to formation of relatively high molecular weight polymers without requiring cross-linking, such as is conventionally introduced by polyols having greater than two hydroxy-functional groups. Examples of polyols useful in the present invention include, but are not limited to, polyester polyols (e.g., lactone polyols) and the alkylene oxide (e.g., ethylene oxide; 1,2-epoxypropane; 1,2-epoxybutane; 2,3-epoxybutane; isobutylene oxide; and epichlorohydrin) adducts thereof, polyether polyols (e.g., polyoxyalkylene polyols, such as polypropylene oxide polyols, polyethylene oxide polyols, polypropylene oxide polyethylene oxide copolymer polyols, and polyoxytetramethylene polyols; polyoxycycloalkylene polyols; polythioethers; and alkylene oxide adducts thereof), polyalkylene polyols, polycarbonate polyols, mixtures thereof, and copolymers therefrom.

Polycarbonate-based polyurethanes are preferred according to one embodiment. It was found that this type of polyurethane chemistry easily facilitated obtainment of polyurethane-based backings with properties desired. See U.S. Pat. No. 4,476,293 for a description of exemplary polycarbonate-based polyurethanes.

In one preferred embodiment, a polycarbonate diol is used to prepare polycarbonate-based polyurethane according to the invention. Although polyols containing more than two hydroxy-functional groups are generally less preferred than diols, certain higher functional polyols may also be used in the present invention. These higher functional polyols may be used alone, or in combination with other isocyanate-reactive materials, for the isocyanate-reactive component.

For broader formulation latitude, at least two isocyanate-reactive materials, such as polyols, may be used for the isocyanate-reactive component. However, as any suitable isocyanate-reactive component can be used to form the polyurethane, much latitude is provided in the overall polyurethane chemistry.

The isocyanate-reactive component is reacted with an isocyanate-functional component during formation of the polyurethane. The isocyanate-functional component may contain one isocyanate-functional material or mixtures thereof. Polyisocyanates, including derivatives thereof (e.g., ureas, biurets, allophanates, dimers and trimers of polyisocyanates, and mixtures thereof), (hereinafter collectively referred to as "polyisocyanates") are the preferred isocyanate-functional materials for the isocyanate-functional component. Polyisocyanates have at least two isocyanate-functional groups and provide urethane linkages when reacted with the preferred hydroxy-functional isocyanate-reactive components. In one embodiment, polyisocyanates useful for preparing polyurethanes are one or a combination of any of the aliphatic or aromatic polyisocyanates commonly used to prepare polyurethanes.

Generally, diisocyanates are the preferred polyisocyanates. Useful diisocyanates include, but are not limited to, aromatic diisocyanates, aromatic-aliphatic diisocyanates, aliphatic diisocyanates, cycloaliphatic diisocyanates, and other compounds terminated by two isocyanate-functional groups (e.g., the diurethane of toluene-2,4-diisocyanate-terminated polypropylene oxide polyol).

Examples of preferred diisocyanates include the following: 2,6-toluene diisocyanate; 2,5-toluene diisocyanate; 2,4-toluene diisocyanate; phenylene diisocyanate; 5-chloro-2,4-toluene diisocyanate; 1-chloromethyl-2,4-diisocyanato benzene; xylylene diisocyanate; tetramethyl-xylylene diisocyanate; 1,4-diisocyanatobutane; 1,6-diisocyanatohexane; 1,12-diisocyanatododecane; 2-methyl-1,5-diisocyanatopentane; methylenedicyclohexylene-4,4'-diisocyanate; 3-isocyanatomethyl-3,5,5'-trimethylcyclohexyl isocyanate (isophorone diisocyanate); 2,2,4-trimethylhexyl diisocyanate; cyclohexylene-1,4-diisocyanate; hexamethylene-1,6-diisocyanate; tetramethylene-1,4-diisocyanate; cyclohexane-1,4-diisocyanate; naphthalene-1,5-diisocyanate; diphenylmethane-4,4'-diisocyanate; hexahydroxylylene diisocyanate; 1,4-benzene diisocyanate; 3,3'-dimethoxy-4,4'-diphenyl diisocyanate; phenylene diisocyanate; isophorone diisocyanate; polymethylene polyphenyl isocyanate; 4,4'-biphenylene diisocyanate; 4-isocyanatocyclohexyl-4'-isocyanatophenyl methane; and p-isocyanatomethyl phenyl isocyanate.

When preparing polyurethane dispersions for casting into layers of polyurethane, the isocyanate-reactive and isocyanate-functional components may optionally be reacted with at least one reactive emulsifying compound according to one embodiment of the invention. The reactive emulsifying compound contains at least one anionic-functional group, cationic-functional group, group that is capable of forming an anionic-functional group or cationic-functional group, or mixtures thereof. This compound acts as an internal emulsifier because it contains at least one ionizable group. Thus, these compounds are referred to as "reactive emulsifying compounds."

Reactive emulsifying compounds are capable of reacting with at least one of the isocyanate-reactive and isocyanate-functional components to become incorporated into the polyurethane. Thus, the reactive emulsifying compound contains at least one, preferably at least two, isocyanate- or active hydrogen-reactive- (e.g., hydroxy-reactive) groups. Isocyanate- and hydroxy-reactive groups include, for example, isocyanate, hydroxyl, mercapto, and amine groups.

Preferably, the reactive emulsifying compound contains at least one anionic-functional group or group that is capable of forming such a group (i.e., an anion-forming group) when reacted with the isocyanate-reactive (e.g., polyol) and isocyanate-functional (e.g., polyisocyanate) components. The anionic-functional or anion-forming groups of the reactive emulsifying compound can be any suitable groups that contribute to ionization of the reactive emulsifying compound. For example, suitable groups include carboxylate, sulfate, sulfonate, phosphate, and similar groups. As an example, dimethylolpropionic acid (DMPA) is a useful reactive emulsifying compound. Furthermore, 2,2-dimethylolbutyric acid, dihydroxymaleic acid, and sulfopolyester diol are other useful reactive emulsifying compounds. Those of ordinary skill in the art will recognize that a wide variety of reactive emulsifying compounds are useful in preparing polyurethanes for backings according to the present invention.

One or more chain extenders can also be used in preparing polyurethanes for backings according to the invention. For example, such chain extenders can be any or a combination of the aliphatic polyols, aliphatic polyamines, or aromatic polyamines conventionally used to prepare polyurethanes.

Illustrative of aliphatic polyols useful as chain extenders include the following: 1,4-butanediol; ethylene glycol; 1,6-hexanediol; glycerine; trimethylolpropane; pentaerythritol; 1,4-cyclohexane dimethanol; and phenyl diethanolamine. Also note that diols such as hydroquinone bis(β-hydroxyethyl)ether; tetrachlorohydroquinone-1,4-bis(β-hydroxyethyl)ether; and tetrachlorohydroquinone-1,4-bis(β-hydroxyethyl)sulfide, even though they contain aromatic rings, are considered to be aliphatic polyols for purposes of the invention. Aliphatic diols of 2-10 carbon atoms are preferred. Especially preferred is 1,4-butanediol.

Illustrative of useful polyamines are one or a combination of the following: p,p'-methylene dianiline and complexes thereof with alkali metal chlorides, bromides, iodides, nitrites and nitrates; 4,4'-methylene bis(2-chloroaniline); dichlorobenzidine; piperazine; 2-methylpiperazine; oxydianiline; hydrazine; ethylenediamine; hexamethylenediamine; xylylenediamine; bis(p-aminocyclohexyl)methane; dimethyl ester of 4,4'-methylenedianthranilic acid; p-phenylenediamine; m-phenylenediamine; 4,4'-methylene bis(2-methoxyaniline); 4,4'-methylene bis(N-methylaniline); 2,4-toluenediamine; 2,6-toluenediamine; benzidine; 3,4'-dimethylbenzidine; 3,3'-dimethoxybenzidine; dianisidine; 1,3-propanediol bis(p-aminobenzoate); isophorone diamine; 1,2-bis(2'-aminophenylthio)ethane; 3,5-diethyl toluene-2,4-diamine; and 3,5-diethyl toluene-2,6-diamine. The amines preferred for use are 4,4'-methylene bis(2-chloroaniline); 1,3-propanediol bis(p-aminobenzoate); and p,p'-methylenedianiline and complexes thereof with alkali metal chlorides, bromides, iodides, and nitrates.

Any suitable additives can be present in conjunction with the base polymer in the backing. Other additives are selected as known to those skilled in the art based on the intended application. Those skilled in the art are readily able to determine the amount of such additives to use for the desired effect.

While the use of certain amounts of crosslinker may still allow formation of extensible backings, if crosslinkers are present, they are generally used in an amount of less than about 4 parts by weight, and preferably less than about 2 parts by weight, based on 100 parts by weight of any polymer crosslinkable therewith prior to any crosslinking reaction. Further, crosslinkers may be present if they are not used in combination with polymers that are crosslinkable therewith or where, if crosslinkable, resulting crosslink density is minimal (e.g., due to minimal reactive sites on the base polymer) so as not to significantly affect extensibility of the backing. In a preferred embodiment, the backing is essentially free of crosslinkers and reaction products thereof (i.e., the backing is essentially uncrosslinked). It was found that the potential benefits imparted by crosslinking such an exterior layer were substantially outweighed by the significantly improved extensibility provided by antimicrobial laminates employing an essentially uncrosslinked backing. As such, crosslinkers and reaction products are not discernible in such preferred embodiments when using chemical analysis.

Any suitable adhesive can be used for the adhesive in antimicrobial laminates according to the invention. In a preferred embodiment, the adhesive comprises a pressure-sensitive adhesive. It is also preferred that the adhesive comprises a skin-compatible adhesive. "Skin-compatible adhesives" of the invention are those that do not lead to statistically significant skin discomfort or skin color change during contact between the adhesive and skin for a period of six hours.

While any suitable chemistry can be used for the base polymer in the adhesive, (meth)acrylate—acrylate and methacrylate—chemistry is preferred. In addition to (meth)acrylate chemistries, other suitable chemistries are known to those skilled in the art and include, for example, those based on synthetic and natural rubbers, polybutadiene and copolymers thereof, polyisoprene or copolymers thereof, and silicones (e.g., polydimethylsiloxane and polymethylphenylsiloxane). Preferably, the base polymer is essentially acid-free (e.g., acid components are not co-polymerized into the base polymer). Any suitable additives can be present in conjunction with the base polymer in the adhesive.

In particular, an adhesive based on 2-ethyl hexyl acrylate and vinyl acetate monomers polymerized as known to those skilled in the art was found useful in one embodiment of the invention. The adhesive can be crosslinked using, for example, conventional aluminum or melamine crosslinkers.

In one embodiment, the adhesive layer has a thickness of about 5 microns to about 150 microns. In a further embodiment, the adhesive layer has a thickness of about 10 microns to about 50 microns. In yet a further embodiment, the adhesive layer has a thickness of about 30 microns to about 100 microns.

For preparation of the adhesive layer, any suitable method can be used. For example, a film of the desired thickness can be cast onto a release film according to one embodiment and as known to those skilled in the art. In one embodiment, the film of adhesive contained on the release film can be laminated to the unsupported side of the carrier layer, after which time the supporting carrier film is removed from the carrier layer for lamination to the backing.

Any suitable method can be used to laminate the backing to the adhesive layer. For example, the backing can be adhered directly to the adhesive layer using thermal bonding. According to this method, a preformed backing is adhered to the adhesive layer and bonded using heat and, optionally, pressure.

According to another embodiment, at least one of the adhesive layer and the backing is formed by direct coating onto the other layer according to conventional methods. No matter what method is used, antimicrobial laminates of the invention can be formed using a continuous or batch process.

Until its application on a surface, the adhesive layer of antimicrobial laminates of the invention can be protected using, for example, a conventional release liner. As such, the laminate can be stored and shipped easily in roll or other forms until its application.

In a preferred embodiment, antimicrobial laminates of the invention are chlorhexidine-containing. Chlorhexidine-containing antimicrobial laminates comprise an antimicrobial amount of chlorhexidine in its pure form (i.e., as a free base) or in the form of at least one chlorhexidine salt. Suitable counterions for chlorhexidine include, but are not limited to, dihydrochloride, methosulfate, lactate, gluconate, acetate, diacetate, and the like. An exemplary chlorhexidine salt is chlorhexidine gluconate (CHG).

In a preferred exemplary embodiment, chlorhexidine is present in its substantially pure form. When using pure chlorhexidine, antimicrobial activity is increased as compared to use of chlorhexidine salts. It is believed that lack of bonding between chlorhexidine and the polymeric material in which it is dispersed (as compared to the at least ionic bonding present when chlorhexidine salts are dispersed in polymeric material) contributes to improved release of chlorhexidine from the polymeric material and, hence, antimicrobial effect.

An antimicrobially effective amount of chlorhexidine is present in the laminate. In one embodiment, the backing of chlorhexidine-containing antimicrobial laminates comprises the antimicrobially effective amount of chlorhexidine. In another embodiment, the adhesive comprises the antimicrobially effective amount of chlorhexidine. In an exemplary embodiment, at least about 3% by weight pure chlorhexidine is present in the adhesive of such a laminate. In a further embodiment, about 8.75% by weight pure chlorhexidine is present in the adhesive of such a laminate.

Advantageously, adhesion of the adhesive containing pure chlorhexidine according to preferred embodiments of the invention is not detrimentally compromised and remains aggressive. For example, when tested against stainless steel according to ASTM D1000, preferred antimicrobial laminates according to the invention have an adhesion level of at least about 30 oz./in. (350 mL/cm), and more preferably an adhesion level of at least about 50 oz./in. (580 mL/cm).

Antimicrobial laminates of the invention, such as surgical drapes, can be applied according to conventional methodology known to those of ordinary skill in the art. In an exemplary embodiment, a skin prepping solution is applied to the skin before the drape is adhered thereto. For example, 3M's DuraPrep Surgical Solution (an iodine povacrylex and isopropyl alcohol solution available from 3M Company of St. Paul, Minn.) or ChloraPrep (a solution containing 2% chlorhexidine gluconate in 70% isopropyl alcohol available from Cardinal Health, Inc. through its Enturia division—Leawood, Kans.) are suitable skin prepping solutions. Recognize, however, that pre-application of a skin prepping solution is optional when applying surgical drapes of the invention. Whether the skin is prepped or not, surgical drapes of the invention are otherwise adhered to a patient's skin according to known methodology.

Exemplary embodiments and applications of the invention are described in the following non-limiting examples.

EXAMPLES

Example 1

Example 5 of U.S. Pat. No. 4,310,509 was modified by using pure chlorhexidine instead of chlorhexidine acetate.

Example 2

First, a 98# polyethylene-coated kraft paper with silicone coated on one side was used as a release liner onto which an adhesive layer was formed. The adhesive layer was formed from an adhesive composition prepared by charging a closed vessel with initial components as follows: 43% by weight 2-ethyl hexyl acrylate and 57% by weight ethyl acetate. The weight percentages of each component were based on total weight of the reaction components, which also included 2% by weight benzoyl peroxide (98%) added to the initial components. Then, the components were charged under a nitrogen atmosphere and using agitation. The vessel was heated at 80° C. until exotherm was reached. The exotherm was maintained by addition of the remaining benzoyl peroxide. After the benzoyl peroxide was depleted and the exotherm was complete, aluminum acetal acetonate was added to the polymerized solution in the amount of 0.2% by weight based on solid weight of the polymer. Further, 8.5% by weight pure chlorhexidine in a solution isopropyl alcohol was then added in the amount of 3.7% by weight based on total weight of the solution.

The adhesive composition, having a percent solids of about 43%, was then coated onto the release liner and dried in a 14-zone oven, at 20 seconds per zone, with the zone temperatures set as follows: zone 1 (50° C.), zone 2 (60° C.), zone 3 (70° C.), zone 4 (80° C.), zone 5 (90° C.), zone 6 (90° C.), zones 7-10 (100° C.), and zones 11-14 (120° C.). With drying, the aluminum acetal acetonate functioned to crosslink the adhesive polymer. The thickness of the adhesive thus formed was 25 microns. The construction was then run through a chill stack to reduce the temperature to about 30° C.

Meanwhile, a 6.25-micron-thick film for the backing was formed on a 76-micron thick (3-mil-thick) silicone-coated polyester carrier film. The film was formed by solution coating the polyurethane-based composition described below on the supporting carrier film. After the composition was coated on the carrier film, it was run through the 14-zone oven and then chilled to about 30° C.

The polyurethane-based composition was prepared by charging a closed vessel with 7.36% by weight of a hybrid linear hexane diol/1,6-polycarbonate polyester having terminal hydroxyl groups, 43.46% by weight toluene, 43.46% by weight isopropyl alcohol, and 0.03% by weight dibutyl tin laureate. The weight percentages of each component were based on total weight of the reaction components, which also included 5.68% by weight isophorone diisocyanate added later. The components were charged under a nitrogen atmosphere and using agitation. After the vessel was heated to 90° C., 5.68% by weight isophorone diisocyanate was continually added to the vessel through the resultant exotherm. After the exotherm was complete, the composition was maintained at 90° C. for one additional hour while still using agitation.

Once the film for the backing and adhesive layer were formed, they were thermally bonded to each other. During thermal bonding, the backing and adhesive layer were contacted for about three seconds with application of heat 150° C. (300° F.) and 140 Pa (20 psi) pressure.

A sample of the antimicrobial laminate thus formed was prepared. For skin-compatibility testing, a 4"×4" (10 cm×10 cm) sample was used as a test specimen. Skin on the back of a subject was prepped for placement of the sample by wiping the skin area with an alcohol wipe. The test specimen was then placed on the prepped area of the back and photographed. After being adhered for about six hours, the test specimen was then photographed again, both before removing the test specimen and then immediately following removal of the test specimen. Comparison of the photographs with each other and with those of a control test specimen prepared according to Comparative Example C1, infra, simultaneously placed on the other side of the subject's back provided confirmation that the adhesive of the laminate was skin-compatible. No irritation was visibly present, and no skin discomfort was reported by the subject.

Another sample of the laminate was tested according to ISO 10993 ("Biological Evaluation of Medical Devices") and yielded a score of "0" on a scale of 0-8 with respect to skin irritation.

Figure 2:
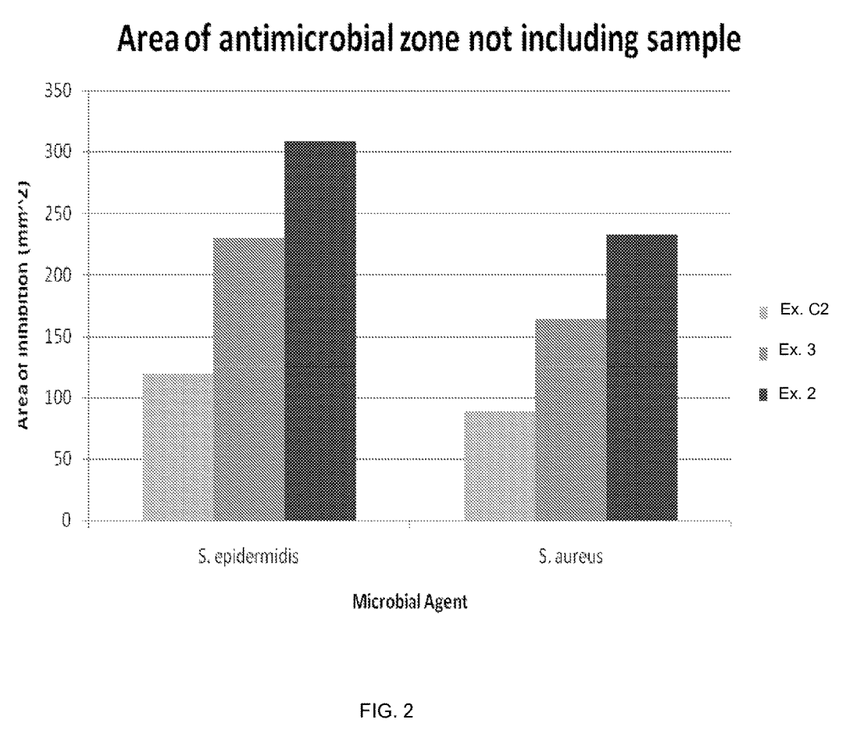
FIG. 2 is a graphical illustration of areas of antimicrobial activity against *S. epidermidis* and *S. aureus* associated with exemplified surgical incise drape materials.

A sample of the material was also tested for antimicrobial properties, with the results illustrated in FIG. 2 ("Ex. 2"). The test procedure followed is outlined in "Antimicrobial Susceptibility Test: Zone of Inhibition" (Doc. No. STP0124) available from Nelson Laboratories (Salt Lake City, Utah).

In addition, ASTM D1000 was used to test adhesion of the sample against a stainless steel substrate. When tested as such, the sample was measured to have an adhesion of 43 oz./in. (500 mL/cm).

Example 3

An antimicrobial laminate was prepared as described in Example 2, except the amount of chlorhexidine in the isopropyl alcohol solution of the adhesive composition was reduced from 8.5% by weight to 3% by weight.

A sample of the laminate thus formed was prepared. For skin-compatibility testing, a 4"×4" (10 cm×10 cm) sample was used as a test specimen. Skin on the back of a subject was prepped for placement of the sample by wiping the skin area with an alcohol wipe. The test specimen was then placed on the prepped area of the back and photographed. After being adhered for about six hours, the test specimen was then photographed again, both before removing the test specimen and then immediately following removal of the test specimen. Comparison of the photographs with each other and with those of a control test specimen prepared according to Comparative Example C1, infra, simultaneously placed on the other side of the subject's back provided confirmation that the adhesive of the laminate was skin-compatible. No irritation was visibly present, and no skin discomfort was reported by the subject.

Another sample was tested according to ISO 10993 ("Biological Evaluation of Medical Devices") and yielded a score of "0" on a scale of 0-8 with respect to skin irritation.

A sample of the material was also tested for antimicrobial properties, with the results illustrated in FIG. 2 ("Ex. 3"). The test procedure followed is outlined in "Antimicrobial Susceptibility Test: Zone of Inhibition" (Doc. No. STP0124) available from Nelson Laboratories (Salt Lake City, Utah).

In addition, ASTM D1000 was used to test adhesion of the sample against a stainless steel substrate. When tested as such, the sample was measured to have an adhesion of 43 oz./in. (500 mL/cm).

Comparative Example C1

An antimicrobial laminate was prepared as described in Example 2, except chlorhexidine was omitted from the adhesive composition.

A sample of the laminate thus formed was prepared. For skin-compatibility testing, a 4"×4" (10 cm×10 cm) sample was used as a test specimen. Skin on the back of a subject was prepped for placement of the sample by wiping the skin area with an alcohol wipe. The test specimen was then placed on the prepped area of the back and photographed. After being adhered for about six hours, the test specimen was then photographed again, both before removing the test specimen and then immediately following removal of the test specimen. Comparison of the photographs with each other and with those of test specimens prepared according to Examples 2 and 3, supra, simultaneously placed on the other side of the subject's back provided confirmation that the adhesive of the laminate was skin-compatible. No irritation was visibly present, and no skin discomfort was reported by the subject.

Another sample was tested according to ISO 10993 ("Biological Evaluation of Medical Devices") and yielded a score of "0" on a scale of 0-8 with respect to skin irritation.

Comparative Example C2

A 3M IOBAN 2 Antimicrobial Incise Drape (available from 3M Company of St. Paul, Minn.) was obtained and tested.

A sample of the drape was tested for antimicrobial properties, with the results illustrated in FIG. 2 ("Ex. C2"). The test procedure followed is outlined in "Antimicrobial Susceptibility Test: Zone of Inhibition" (Doc. No. STP0124) available from Nelson Laboratories (Salt Lake City, Utah).

Various modifications and alterations of the invention will become apparent to those skilled in the art without departing from the spirit and scope of the invention, which is defined by the accompanying claims. It should be noted that steps recited in any method claims below do not necessarily need to be performed in the order that they are recited. Those of ordinary skill in the art will recognize variations in performing the steps from the order in which they are recited. In addition, the lack of mention or discussion of a feature, step, or component provides the basis for claims where the absent feature or component is excluded by way of a proviso or similar claim language.

Further, as used throughout, ranges may be used as shorthand for describing each and every value that is within the range. Any value within the range can be selected as the terminus of the range. Similarly, any discrete value within the range can be selected as the minimum or maximum value recited in describing and claiming features of the invention.

In addition, as discussed herein it is again noted that compositions described herein may comprise all components in one or multiple parts. Further, while reference may be made herein to preparation of the various intermediate components, recognize that some such intermediate components may be commercially available and, as such, can be used according to the invention as an alternative to otherwise preparing the same. Other variations are recognizable to those of ordinary skill in the art.

The invention claimed is:

1. An antimicrobial laminate comprising:
   at least one adhesive layer;
   a backing on a first side of the adhesive layer; and
   optionally, a release liner on a second side of the adhesive layer opposite from the first side of the adhesive layer,
   wherein at least one of the adhesive layer and the backing comprises an antimicrobially effective amount of substantially pure chlorhexidine as a free base dispersed within a polymeric material,
   wherein a lack of bonding between chlorhexidine and the polymeric material in which it is dispersed exists, and
      wherein the adhesive layer comprises at least about 3% by weight of the substantially pure chlorhexidine.

2. The antimicrobial laminate of claim 1, wherein the laminate is a surgical incise drape.

3. The antimicrobial laminate of claim 1, wherein the laminate essentially comprises substantially transparent or translucent flexible polymeric materials.

4. The antimicrobial laminate of claim 1, wherein the backing imparts structural integrity to the laminate.

5. The antimicrobial laminate of claim 1, wherein the backing is extensible.

6. The antimicrobial laminate of claim 1, wherein the backing comprises a polyurethane base polymer.

7. The antimicrobial laminate of claim 1, wherein the at least one adhesive layer comprises a pressure-sensitive adhesive.

8. The antimicrobial laminate of claim 1, wherein the at least one adhesive layer comprises a skin-compatible adhesive.

9. The antimicrobial laminate of claim 1, wherein the at least one adhesive layer comprises a (meth)acrylate adhesive.

10. The antimicrobial laminate of claim 1, wherein the laminate is essentially free of chlorhexidine salt.

11. The antimicrobial laminate of claim 1, wherein the at least one adhesive layer is essentially free of antimicrobial agents.

12. The antimicrobial laminate of claim 1, wherein the backing is essentially free of antimicrobial agents.

13. The antimicrobial laminate of claim 1, wherein the at least one adhesive layer comprises the antimicrobially effective amount of substantially pure chlorhexidine.

14. The antimicrobial laminate of claim 1, wherein the at least one adhesive layer comprises about 8.75% by weight of the substantially pure chlorhexidine.

15. The antimicrobial laminate of claim 1, wherein, when the laminate is tested against stainless steel according to ASTM D1000, the laminate has an adhesion level of at least about 350 mL/cm.

16. The antimicrobial laminate of claim 1, wherein, when the laminate is tested against stainless steel according to ASTM D1000, the laminate has an adhesion level of at least about 580 mL/cm.

17. The antimicrobial laminate of claim 1 in which antimicrobial agents in the antimicrobial laminate consist of the substantially pure chlorhexidine as a free base dispersed within a polymeric material.

18. The antimicrobial laminate of claim 1, wherein a base polymer in the adhesive layer is essentially acid-free.

19. The antimicrobial laminate of claim 18, wherein the adhesive layer comprises the antimicrobially effective amount of the substantially pure chlorhexidine as a free base dispersed within the polymeric material.

20. An antimicrobial laminate comprising:
at least one adhesive layer;
a backing on a first side of the adhesive layer; and
optionally, a release liner on a second side of the adhesive layer opposite from the first side of the adhesive layer,
wherein at least one of the adhesive layer and the backing comprises an antimicrobially effective amount of substantially pure chlorhexidine as a free base dispersed within a polymeric material, and
wherein the adhesive layer comprises a (meth)acrylate adhesive and at least about 3% by weight of the substantially pure chlorhexidine.

* * * * *